United States Patent [19]

Agrawal

[11] Patent Number: 4,914,237

[45] Date of Patent: Apr. 3, 1990

[54] ALKYLATION OF TOLUENEDIAMINE AND PARA-PHENYLENEDIAMINE WITH ISOBUTYLENE IN THE PRESENCE OF ACIDIC, CRYSTALLINE MOLECULAR SIEVES

[75] Inventor: Rakesh Agrawal, Allentown, Pa.

[73] Assignee: Air Products and Chemicals, Inc., Allentown, Pa.

[21] Appl. No.: 277,096

[22] Filed: Nov. 29, 1988

[51] Int. Cl.[4] ...................... C07C 85/24; C07C 87/58; B01J 29/38

[52] U.S. Cl. ...................................... 564/409; 502/30; 502/31; 502/55; 564/305

[58] Field of Search ............................ 502/30, 31, 55; 564/409, 305

[56] References Cited

U.S. PATENT DOCUMENTS

| | | | |
|---|---|---|---|
| 3,546,100 | 12/1970 | Yan | 208/111 |
| 3,670,030 | 6/1972 | Sparks | 564/409 |
| 4,740,620 | 4/1988 | Dixon et al. | 564/409 |
| 4,745,223 | 5/1988 | Burgoyne et al. | 564/305 |
| 4,760,184 | 7/1988 | Pierantozzi | 564/409 |
| 4,851,579 | 7/1989 | Pierantozzi | 564/409 |

FOREIGN PATENT DOCUMENTS

| | | | |
|---|---|---|---|
| 0202557 | 11/1986 | European Pat. Off. | 564/409 |
| 1051271 | 2/1959 | Fed. Rep. of Germany . | |
| 1406739 | 6/1965 | France . | |
| 6407636 | 1/1966 | Netherlands . | |
| 414574 | 8/1934 | United Kingdom . | |
| 846226 | 8/1960 | United Kingdom . | |

*Primary Examiner*—Paul E. Konopka

*Attorney, Agent, or Firm*—Russell L. Brewer; James C. Simmons; William F. Marsh

[57] ABSTRACT

This invention relates to an improvement in a fixed bed process for producing tert-butyl-derivatives of aromatic amines, e.g., para-phenylenediamine and toluenediamine by the reaction of isobutylene with the corresponding aromatic diamine in the presence of a highly acidic crystalline alumino-silicate catalyst. The improvement for regenerating the catalyst during operation constitutes adding sufficient water to the catalyst to provide sufficient saturation of the catalyst during the reaction and generally retard the reaction and then substantially decreasing the quantity of added water or reducing the amount of water added.

9 Claims, No Drawings

ALKYLATION OF TOLUENEDIAMINE AND PARA-PHENYLENEDIAMINE WITH ISOBUTYLENE IN THE PRESENCE OF ACIDIC, CRYSTALLINE MOLECULAR SIEVES

TECHNICAL FIELD

This invention pertains to an improved process for alkylating toluenediamine and para-phenylenediamines in the presence of crystalline molecular sieve catalysts.

BACKGROUND OF THE INVENTION

Processes for alkylating a variety of alkylatable aromatic compounds by contacting such compounds with a hydrocarbon radical providing source such as an olefin or alcohol are widely known. Typically, alklatable aromatic compounds are mononuclear aromatic compounds themselves or those substituted with a hydroxyl, a mine or an ether group. The alkylation has been carried out in the presence of homogeneous and heterogeneous catalyst systems.

Representative references which illustrate some of the early processes in forming ring alkylated aromatic amines are:

British Patent 414,574 discloses the reaction of aniline with various olefins, e.g., cyclohexene and alcohols, e.g., butanol in the presence of a neutral or weakly acidic catalyst system commonly referred to as hydrosilicates at temperatures from 200°-270° C. Ortho and para-cyclohexylaniline, N-cyclohexylaniline, N-butylaniline and para-methyl-ortho-cyclohexylaniline and N-cyclohexyl-para-toluidine are listed as representative products.

British Patent 846,226 discloses ring alkylation of aromatic amines with olefins using active, substantially neutral bleaching earths of the montmorillonite type as a catalyst.

As 1,051,271 discloses the ring alkylation of aniline with an olefin, e.g., ethylene, in the presence of kaolin or in the presence of aluminum and aluminum alloys. Alkylation with higher olefins, e.g., propylene, butylene, etc., was carried out in the presence of Friedel-Crafts catalysts or bleaching earths under liquid phase conditions at temperatures from 150°-350° C. Representative examples of operable catalytic systems including aluminum chloride, zinc chloride, boron trifluoride, sulfuric acid, phosphoric acid and bleaching earth. Ring alkylation at the ortho-position was predominant, although other products such as the di and tri-alkylated aniline product were produced.

Netherlands Application 6,407,636 has recognized that alkylation of various aromatic and heterocyclic compounds can be carried out in the presence of a zeolite having a pore size from 6-15 Angstroms wherein active cationic sites are obtained with an exchangeable metal or hydrogen cations in their ordered internal structure. Alkylating agents include olefins having from 1 to 12 carbon atoms, alkyl halides such as propyl bromide and ethyl chloride; and alkanols, such as, methanol, ethanol, and propanol. Various compounds were suggested as being suited for alkylation and these include both the heterocyclic and aromatic ring compounds. For aromatic amine alkylation it was suggested that a zeolite with a disperse distribution of acid sites should be utilized. It was believed the highly acidic zeolite catalysts which have a high density of acidic sites may bind the amine to the catalyst and block the pore structures. In Example 1, aniline was alkylated with propylene using sodium zeolite X having a pore size of 13 Angstroms and numerous alkylated amines were produced. Example 3 shows alkylation of diphenylamine with cyclohexene using a rare earth exchanged 13× zeolite. Again, numerous ring alkylated products were produced and high temperatures, e.g., 300° C. and above apparently being required to weaken the amine-acid bond.

French Patent 1,406,739, which is equivalent to Netherlands Application 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13× which has undergone a partial exchange with rare earth metals and having a pore size of 13Å.

U.S. Pat. No. 4,745,223 discloses the preparation of tert-alkyl toluenediamines and other aromatic amines by reacting an olefin with an aromatic amine in the presence of a highly acidic crystalline alumino-silicate. Examples of aromatic diamines include tert-butyltoluenediamine.

U.S. Pat. No. 3,670,030 discloses the alkylation of a phenolic compound with an olefin in contact with an alumina catalyst. To prevent deactivation of the catalyst, water was added to the reaction zone in a controlled amount, e.g., from about 500-3000 ppm based upon the phenolic compound.

U.S. Pat. No. 3,546,100 shows a process for cracking hydrocarbon feedstocks over a rare earth exchanged crystalline alumina-silicate catalyst. Water addition to the reaction was made in order to control catalyst activity.

SUMMARY OF THE INVENTION

This invention pertains to an improved fixed bed catalytic process for effecting alkylation of an aromatic diamine, i.e., toluenediamine and para-phenylenediamine with isobutylene. The basic fixed bed process comprises contacting the aromatic diamine with isobutylene in the presence of an acidic crystalline alumino-silicate catalyst under conditions for effecting alkylation. The improvement resides in regenerating the alumino-silicate catalyst during operation and comprises contacting the catalyst with water in sufficient amount to saturate the catalyst and then reducing flow.

Some of the advantages associated with this invention include:

- an ability to effect alkylation at high conversion over extended reaction times:
- an ability to effect and maintain ring alkylation at high rates;
- an ability to minimize formation of dialkylated toluenediamine by-products;
- an ability to regenerate the catalyst in fixed-bed operation without shutdown or through special regeneration equipment.

DETAILED DESCRIPTION OF THE INVENTION

As has been observed from plant runs, crystalline alumino-silicates deactivate during the alkylation of certain aromatic diamines, these being toluenediamine and para-phenylenediamine, with isobutylene. In some cases, catalyst deactivation occurs with other olefins although the catalyst does not respond with water treatment to be described; and in other cases, the aromatic amines, e.g., meta-phenylenediamine does not deactivate rapidly as does para-phenylenediamine or toluenediamine in the reaction with isobutylene. However, deactivate may occur with the alkylation of meta-phenylenediamine on reaction with cyclopentadiene but the catalyst does not respond or regenerate with water treatment.

In the alkylation of aromatic amines used in this invention, toluenediamine and para-phenylenediamine, the olefin to amine molar ratios will range from about 1 to 20 moles olefin per mole of the aromatic amine and preferably about 2–4 moles olefin per mole of the aromatic amine.

The catalysts useful in the reaction of the present invention are those crystalline molecular sieves which are solid phase and have an acidity factor of at least 0.30 and preferably at least 1 and referred to in U.S. Pat. No. 4,740,620 and are incorporated by reference. More specifically, these highly acidic molecular sieves have sufficient catalytic activity to effect ring-alkylation of the aromatic amine in high conversion (based upon amine) and in high selectivity. The crystalline molecular sieves include crystalline alumino-silicates, commonly referred to as zeolites, and they can be of both natural and synthetic material. Some of the zeolites are faujasite and mordenite. When initially prepared, the cation in the crystalline alumino-silicate usually is an alkali metal, typically sodium. This ion must be exchanged in sufficient proportion, generally in excess of 60%, with an acidic ion such as a rate earth metal, e.g. lanthanum, cerium, praseodymium; hydrogen or some of the transition metals such as nickel, copper, chromium and the like for the practice of this invention. The substitution of various ions for the sodium ion alters the acidity of the zeolite thus making it more reactive and catalytically effective for ring alkylation of the aromatic amine.

The naturally occurring and synthetic zeolites normally have a silica to alumina molar ratio of from 2 to 15:1. The acidity of the zeolite may be altered by a technique called dealumination. In effect, the practice of dealumination decreases the alumina ratio. The removal of alumina from the internal structure can also enlarge the cage structure or pore size of the zeolite to permit entry of and diffusion of larger molecules into its internal structure. It can also have a tendency to increase catalyst acidity. Thus, one may be able to utilize a particular cation in a dealuminated zeolite but not use the same cation in its non-dealuminated counterpart since that catalyst would not meet the acidic requirements of this invention. Some of the techniques for dealumination include chelation, dehydration or acidification, the latter which entails the treatment of the zeolite with an inorganic acid. Such techniques for dealumination of zeolite are well known.

The zeolites are porous materials with the pores having generally uniform molecular dimensions. Cavities or cages are formed in the zeolite and are connected by channels of generally defined diameter. For the practice of this invention the cage diameter should be sufficiently large to permit the molecules to effectively enter the interior of the alumino-silicate for reaction and to exit as final product. Typically the pore size will range from about 5 to 15 Angstroms but the size of the pore required can vary depending upon the product being produced.

Molecular sieves have been developed which have been defined as nonzeolites but perform similarly in some reactions to zeolitic materials. They have a cage structure and typically contain alumina and silica in combination with other components, e.g., phosphorus, titania, etc. Representative crystalline molecular sieves are described in U.S. Pat. No. 4,440,871, European patent 124119 and European patent 121232 and are incorporated by reference. For purposes of this invention, these molecular sieves are deemed equivalent to and are to be included within the term crystalline molecular sieves.

Other nonalumino-silicate zeolites which can be used in the practice of the invention are the boron containing zeolites, e.g., borosilicates and borogermanates.

Sufficient alkali metal must be exchanged with appropriate acidic cations to render the crystalline molecular sieve acidic as defined by an acidity factor. This factor is determined by an ammonia absorption/desorption technique which involves treating the catalyst with ammonia at room temperature and then desorbing by heating to a temperature from ambient at 200° C. at 10°/minute, then holding at 200° C. for 2 hours. The amount of ammonia irreversibly adsorbed at 200° C. is indicative of acidity and indicative of the strength of the amine/acid bond. An acidity factor of 0.30 millimoles ammonia irreversibly adsorbed per gram of catalyst at 200° C. is usually necessary to obtain high catalytic activity.

The alkylation of the aromatic amines to effect ring alkylation of the aromatic amine is carried out in a fixed bed reactor with the reactants being fed downflow or upflow through the reactor. Temperatures from 100° to 250° C., preferably 150°–220° C., and pressures of from 50 to 3000 psig, preferably 250–1500 psig are utilized.

One of the problems associated with the utilization of highly acidic crystalline alumino-silicate as a catalyst for the alkylation of toluenediamine and para-phenylenediamine with isobutylene as the alkylating reagent in fixed bed catalytic operation, and in batch operation, is that the catalyst deactivates rapidly. The reaction profile is such that the catalyst is extremely active and selective under initial operating conditions but deactivates quickly to a point where the catalyst must be regenerated. Process control becomes extremely difficult over time. The exact mechanism of deactivation is not fully understood, but it is believed there may be some polymerization of the olefin, formation of tars from by-products or impurities in the toluenediamine or para-phenylenediamine feedstock, reduced solubility of the alkylated aromatic diamine in the feed, or amine salt formation. Nonetheless the catalyst must be frequently regenerated if process control is to be maintained. In contrast, such catalysts used in the alkylation of other aromatic amines e.g., aniline or meta-phenylenediamine with $C_{2-4}$ olefins, such as propylene, do not deactivate nor does deactivation of the catalyst occur in the alkylation of toluenediamine with propylene.

It has been found, in contrast to some reactions associated with the alkylation of aromatic amines that the addition of water to the reaction zone can regenerate the catalyst and enhance catalyst life without substantially and adversely affecting conversion or selectivity. Sufficient water is added to the catalyst to effect saturation of the catalyst during contact with the aromatic diamine and olefin. Saturation or equilibration can be determined by monitoring reaction profiles and usually saturation is indicated by a decrease in conversion. Typically, a conversion decrease of 3-5 mole % is preferred and water addition or injection into the reactor being made over a period of time to maintain this conversion. From about 0.5 to 5.0 moles water per mole aromatic amine and preferably from about 1-3 moles water/mole aromatic amine is required. After water addition has been made to the reactor and the catalyst saturated with water, water addition may be reduced and preferably terminated. Typically, water flow is reduced to a level of about 0 to 0.5 moles water/mole TDA. When the amount of water is reduced, catalyst activity increases because of regeneration and activity approaches that of fresh catalyst. Usually water addition is in excess of 60 minutes and is followed by reduction and preferably termination times of 50 to 500 hours. When the reaction is run in batch mode in a stirred vessel, the use of water in sufficiently large quantities, in intermittent batches can be used to regenerate catalyst. After the reaction, water is discharged with the rest of the reaction products and thus regenerated catalyst is used for batch reaction without any or with very little water.

The following examples are provided to illustrate various embodiments of the invention and are not intended to restrict the scope thereof.

EXAMPLE 1

Preparation of tert-Butyl-toluenediamine via Fixed Bed Reactor

Prior Art—Comparison

A commercial H-Y zeolite (catalyst base LZ-Y82 powder, manufactured by Union Carbide) was used without any pretreatment. The catalyst base LZ-Y82 is an ammonium exchanged powder form of a thermally-stabilized Linde type Y molecular sieve. It has a low level of sodium cations and excellent hydrothermal stability.

The catalyst was obtained as a powder which was pelletized in a press and then crush and sieved to yield 12-18 mesh particles. Fifteen grams of this material were packed between retaining quartz beds in a stainless steel (SS-316) reactor tube of 0.44 inches internal diameter and 36 inches in length.

The toluenediamine (TDA)-isobutylene alkylation reaction was conducted in a continuous flow isothermal mode with downflow of the reactants. The TDA isomer used in the reaction was 2,4-TDA. More specific procedures used in the experiment are outlined below.

The reactor tube was heated to about 125° C. under nitrogen, and then molten TDA at about 130° C. was introduced. After the passage of a sufficient amount of TDA through the reactor, the flow of isobutylene was started to maintain a molar ratio of isobutylene (R) to TDA (R/N ratio) of about 1.2:1. The temperature was maintained at about 125° C. until the mixture of TDA and isobutylene flowed through the entire catalyst bed after which the temperature was increased in stages to the desired value of 180° C. Table 1 sets forth conditions and results.

TABLE 1

2,4-TDA/Isobutylene Alkylation Over LZ-Y82
Bases: Catalyst - 15 g LZ-Y82
T~180° C.
P~550 psig
R/N~1.3:1

| Time On Stream (h) | WHSV[1] ($h^{-1}$) | TDA Conversion (%) | Molar Selectivities (%)[2] TBTDA | NTBTDA | DTBTDA |
|---|---|---|---|---|---|
| 22 | 0.50 | 59 | 85.2 | 13.1 | 1.6 |
| 78 | 0.40 | 32 | 74.3 | 25.4 | 0.2 |
| 127 | 0.40 | 28 | 71.9 | 27.9 | 0.2 |
| 145 | 0.21 | 33 | 73.8 | 25.9 | 0.3 |

[1]WHSV is the weight hourly space velocity defined as g TDA per g catalyst per hour.
[2]TBTDA denotes monotertiarybutyl toluene diamine which consists of 5-tertiarybutyl-2,4-TDA. NTBTDA denotes N-monotertiarybutyl TDA which consists of 2N-tertiarybutyl-2,4-TDA and 4N-tertiarybutyl-2,4-TDA. DTBTDA denotes ditertiarybutyl TDA which consists of 2N,5-ditertiarybutyl-2,4-TDA, 4N,5-ditertiarybutyl-2,4-TDA, and 2N,4N-ditertiarybutyl-2,4-TDA.

From the above data, it can be seen that deactivation of the H-Y zeolite in the fixed bed reactor occurred in the alkylation of 2,4-TDA with isobutylene. At 127 hours when conversion had dropped to about 28%, an attempt to increase TDA conversion by reducing TDA flow was made. That adjustment was unsuccessful in that conversion increase was minimal. Regeneration of the catalyst was required in order to increase activity of the catalyst.

EXAMPLE 2

Preparation of tert-Butyl 2,4-TDA with Water Addition

The procedure of Example 1 was essentially repeated except 12-18 mesh particles were stored over for four days at room temperature. This was done to insure that the zeolite particles were saturated with adsorbed water at room temperature. Then, approximately 9.5 g of this zeolite were packed into the column. Nitrogen gas used to purge and create an inert blanket inside the reactor was presaturated by bubbling through water at room temperature. Table 2 sets forth conditions and results.

TABLE 2

2,4-TDA/Isobutylene Alkylation over LZ-Y82
Bases: 9.5 g LZ-Y82
T~180° C.
P~575 psig
R/N~1.5:1

| Time On Stream (h) | Water/TDA Molar Ratio | WHSV ($h^{-1}$) | TDA Conversion (%) | Molar Selectives (%) TBTDA | NTBTDA | DTBTDA |
|---|---|---|---|---|---|---|
| 26 | 0 | 0.43 | 62 | 82.4 | 15.6 | 1.9 |
| 73 | 0 | 0.39 | 30 | 72.2 | 27.6 | 0.2 |
| 73 | Start $H_2O$ Cofeed | — | — | — | — | — |

TABLE 2-continued 2,4-TDA/Isobutylene Alkylation over LZ-Y82
Bases: 9.5 g LZ-Y82
T~180° C.
P~575 psig
R/N~1.5:1

| Time On Stream (h) | Water/TDA Molar Ratio | WHSV ($h^{-1}$) | TDA Conversion (%) | Molar Selectives (%) TBTDA | NTBTDA | DTBTDA |
|---|---|---|---|---|---|---|
| 170 | 1.6 | 0.43 | 37 | 80.7 | 17.3 | 2.1 |
| 214 | Stop $H_2O$ Cofeed | — | — | — | — | — |
| 236 | 0 | 0.26 | 65 | 82.5 | 12.8 | 4.7 |

It is observed that the initial activity and deactivation profile of this catalyst bed up to 73 hours on stream is very similar to that shown in Table 1 of Example 1. It is believed this is because the zeolite particles (12–18 mesh), which are prepared from powder in ambient air in the lab, adsorb moisture from the air and become nearly saturated with adsorbed water.

At 73 hours on stream, when the catalyst bed had already substantially deactivated, a cofeed of water to the reactor was started. A water to TDA molar ratio was maintained between 1.5 to 3:1. A data point collected at 170 hours on stream shows a TDA conversion of 37% at a TDA WHSV of 0.43 $h^{-1}$. When compared to 30% conversion at a lower WHSV of 0.39 $h^{-1}$ at 73 hours on stream, this clearly shows that some regeneration of the deactivated catalyst bed had occurred. The extent of the regeneration is substantially more than what it appears to be at first glance when it is noted that the presence of such large quantities of water lowers the concentration of isobutylene in the liquid phase by several fold. The reduction in isobutylene concentration in the TDA rich liquid phase would be expected to lower the TDA conversion and most likely does at the 75+ hour stream time, however, because of the regeneration over the next 100 hours of operation, conversion increased from 30% to 37%.

At 214 hours on stream, the water cofeed to the reactor was stopped and the flow of the other reactants was maintained. At 236 hours on stream, a TDA conversion of 65% at WHSV of 0.26 $h^{-1}$ was observed! This conversion is very high because a thermodynamic estimation shows that under the operating conditions employed, this conversion is extremely close to the equilibrium conversion. Furthermore, when the conversion of 65% at 236 hours on stream is compared with the conversion of 33% at 145 hour on stream in Table 1 (Example 1), the extent to which a water cofeed reactivated the deactivated catalyst is clearly evident.

EXAMPLE 3

Preparation of tert-Butyl 2,4-TDA with Water Addition

The procedure of Example 1 was repeated except that water was added incrementally over time and at various levels based on TDA. Table 3 sets forth conditions and results.

TABLE 3

2,4-TDA/Isobutylene Alkylation over LZ-Y82
Bases: 17.9 g LZ-Y82
T~180° C.
P~550 psig
R/N~1.3-1.8:1

| Time On Stream (h) | Water/TDA Molar Ratio | WHSV ($h^{-1}$) | TDA Conversion (%) | Molar Selectivities (%) TBTDA | NTBTDA | DTBTDA |
|---|---|---|---|---|---|---|
| 24 | 0.35 | 0.24 | 57 | 82.7 | 12.6 | 4.7 |
| 65 | 0.32 | 0.26 | 52 | 83.8 | 13.7 | 2.6 |
| 185 | 0.35 | 0.24 | 42 | 81.7 | 16.9 | 1.5 |
| 302 | 0.32 | 0.26 | 39 | 81.3 | 17.8 | 0.9 |
| 302 | Water Flow Stopped | | | | | |
| 323 | 0 | 0.27 | 41 | 79.4 | 20.2 | 0.4 |
| 347 | 0 | 0.27 | 33 | 75.8 | 23.9 | 0.3 |
| 364 | 0 | 0.26 | 32 | 74.5 | 25.2 | 0.3 |
| 364–383 | Regeneration by water without any reactant flow | | | | | |
| 406 | 0 | 0.30 | 42 | 80.6 | 18.4 | 0.9 |
| 429 | 0 | 0.31 | 21 | 67.8 | 31.9 | 0.3 |
| 431 | Water cofeed started at $H_2O$/TDA molar ratio ≃ 0.3 | | | | | |
| 501 | 0.26 | 0.24 | 34 | 76.8 | 22.7 | 0.5 |
| 502 | $H_2O$/TDA molar ratio increased ≃ 1.7 | | | | | |
| 519 | 1.77 | 0.29 | 32 | 82 | 16.7 | 1.4 |
| 547 | $H_2O$/TDA molar ratio decreased to ≃ 0.3 | | | | | |
| 569 | 0.20 | 0.28 | 50 | 83.2 | 15.1 | 1.7 |
| 689 | 0.32 | 0.25 | 44 | 82.4 | 16.7 | 0.9 |
| 782 | 0.24 | 0.25 | 41 | 80.3 | 18.8 | 0.9 |

It is interesting to compare the results of Example 1 from the first 302 hours of this run with those of Table 1. From Table 3, it can be seen that the initial productivity (at 24 hours on stream) of the catalyst bed is less than half of that in Table 1 (at 22 hour on stream). This clearly shows that the presence of water, even in low quantities, decreases the TDA conversion obtained from the reactor. At long times on stream, however, cofeeding of water was beneficial because it decreased the rate of deactivation of the LZ-Y82 catalyst. At 185 hours on stream, a TDA conversion of 42% was obtained at a TDA WHSV of 0.24 $h^{-1}$. This catalytic activity is higher than the 33% TDA conversion for WHSV of 0.21 $h^{-1}$ at 145 hours on stream in Table 1. As the data after 302 hours on stream in Table 3 indicates, the rate of deactivation of the catalyst bed after the initial 185 hours was considerably reduced.

At 302 hours on stream, the water cofeed through the reactor was stopped. A small increase in the TDA conversion from 39% to 41% was observed. This small increase in rate indicates that a small proportion of $H_2O$/TDA in the reactor was unable to keep the catalyst very active (as compared to Example 2). In the absence of a water cofeed, the catalyst bed started to decrease in activity rapidly and at 364 hour on stream at TDA conversion of only 32% at WHSV of 0.26 $h^{-1}$ was obtained.

At 364 hours on stream, when the catalyst had substantially deactivated, an attempt to regenerate it by using only water in the absence of feed was made. The flow rate of both TDA and isobutylene through the reactor was stopped and water was fed for the next 19 hours at 180° C. and 400 psig. After that, the flow of water was stopped and TDA and isobutylene were reintroduced to the reactor. It was seen that after 23 hours (406 hours total time on stream), a TDA conversion of 42% at a WHSV of 0.3 $h^{-1}$ was obtained. Although the TDA conversion was higher than at 364 hours on stream and, even water by itself can regenerate some of the activity of a deactivated LZ-Y82 catalyst bed, this regenerated activity was quickly lost over the next twenty-four hours. This is evidenced by a TDA conversion of only 21% at a TDA WHSV of 0.31 $h^{-1}$ was obtained at 429 hours on stream.

Once the catalyst bed had deactivated again, a cofeed of water through the catalyst bed was started such that the $H_2O$/TDA molar ratio was around 0.3. This molar ratio was similar to that used at the start of this run. It is observed that over the next 70 hours, the activity of the catalyst bed increased somewhat and a TDA conversion of 34% for a TDA WHSV of 0.24 $hr^{-1}$ was obtained (at 501 hours on stream). However, this regeneration was not very effective because in the early part of the run at 185 hours on stream, a TDA conversion of 42% was obtained for the same WHSV.

After about 72 hours with $H_2O$/TDA molar ratio of about 0.3 or at 502 hours the water flow rate to the reactor was increased to provide 1.7 moles water per mole TDA. A sample collected after 17 hours showed a TDA conversion of 32% for a TDA WHSV of 0.29 $h^{-1}$. The reactor was operated in this condition for the next 28 hours, and then the $H_2O$/TDA molar ratio was again decreased to 0.3 by decreasing the water flow (at 547 hours on stream). A sample was collected 22 hours later indicated the TDA conversion was 50% at TDA WHSV of 0.28 $h^{-1}$. This activity is similar to that obtained at the beginning of this run after about 65 hours on stream (52% conversion at WHSV of 0.26 $h^{-1}$). Over the next 120–200 hours, the catalyst bed showed a performance similar to that observed in the early part of this run; i.e., from 65–302 hours on stream.

Rough calculations on the data reported in Table 3 leads to other interesting observations. At 302 hours on stream, when the deactivation rate of the catalyst bed was relatively small, the production rate of TBTDA was about 2.14 g/h. When the flow rate of water to the reactor was increased such that the $H_2O$/TDA molar ratio was about 1.77 at 519 hours, the TBTDA production rate was estimated from the data to be 1.99 g/h. This high water flow rate was continued for the next 45 hours and then dropped back to an $H_2O$/TDA molar ratio of about 0.3. The total loss in TBTDA production during the 45 hours at high water flow rate as about 6.8 g. However, at the end of the 45 hours high water flow rate period, and when the $H_2O$/TDA ratio was dropped to 0.3, the TBTDA production rate increased to be 3.05 g/h (estimated from the data at 569 hours on stream). The production rate of 3.05 g/h was much higher than the original production rate of 2.14 g/h and thus, it would only take an additional 8 hours to make up for the 6.8 g lost during the period of high water flow. After that period, for the next 150–200 hours, the production rate was higher than 2.14 g/h. Accordingly, to optimize an operation, it is recommended that once the production rate drops below a reasonable value, the catalyst bed should be regenerated by cofeeding a larger proportion of water to the reactor, then decreasing or terminating water flow. This operating strategy will provide a higher overall time averaged production rate for TBTDA.

What is claimed is:

1. In a fixed bed process for producing ring alkylated toluenediamine and para-phenylenediamine amines by the reaction of toluenediamine or paraphenylenediamine with isobutylene in the presence of an acidic crystalline alumino-silicate catalyst, the improvement for effecting catalyst regeneration during the ring alkylation of said toluenediamine or paraphenylenediamine which comprises contacting the catalyst with water in an amount sufficient to saturate the catalyst but insufficient for substantially retarding the reaction and then reducing water addition.

2. The process of claim 1 wherein the aromatic amine is toluenediamine.

3. The process of claim 2 wherein the mole ratio of isobutylene to toluenediamine is from about 2 to 4 moles isobutylene per mole toluenediamine.

4. The process of claim 1 wherein the water is added in an amount of from about 0.5 to 5.0 moles water per mole of aromatic amine charged to the reactor.

5. The process of claim 4 wherein the reaction temperature is maintained from 150° to 220° C. and the reaction pressure is maintained from 50 to 3000 psig.

6. The process of claim 5 wherein water is added periodically to the alkylation reaction.

7. The process of claim 5 wherein water is added at a level from about 1 to 3 moles water/mole toluenediamine.

8. The process of claim 7 wherein water is added for a period of at least 1 hour prior to reducing water addition to a level of from 0 to 0.5 moles/mole of TDA.

9. The process of claim 7 wherein the catalyst is an H-Y zeolite.

* * * * *